(12) United States Patent
Yamasaki

(10) Patent No.: US 7,751,603 B2
(45) Date of Patent: Jul. 6, 2010

(54) MEDICAL IMAGE OUTPUT SYSTEM, MEDICAL IMAGE TRANSFERRING APPARATUS AND PROGRAM

(75) Inventor: Toshio Yamasaki, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 1220 days.

(21) Appl. No.: 11/324,266

(22) Filed: Jan. 4, 2006

(65) Prior Publication Data

US 2006/0184555 A1 Aug. 17, 2006

(30) Foreign Application Priority Data

Jan. 5, 2005 (JP) ............... 2005-000756

(51) Int. Cl.
*G06K 9/00* (2006.01)
*G06F 17/00* (2006.01)

(52) U.S. Cl. ..................... 382/128; 707/101

(58) Field of Classification Search ............... 382/128, 382/129, 130, 131, 132, 133, 134; 378/4, 378/21–27, 37, 901; 600/407, 410, 425, 600/427; 250/318, 369, 428, 433; 707/100, 707/101, 102, 104.1
See application file for complete search history.

(56) References Cited

U.S. PATENT DOCUMENTS 5,651,362 A * 7/1997 Shigyo et al. ............... 600/425
6,198,837 B1 * 3/2001 Sasano et al. ............... 382/132

* cited by examiner

*Primary Examiner*—Abolfazl Tabatabai
(74) *Attorney, Agent, or Firm*—Finnegan, Henderson, Farabow, Garrett & Dunner, L.L.P.

(57) ABSTRACT

A medical image output system includes: a medical image transferring apparatus and plural medical image forming apparatus. Each medical image forming apparatus includes a storage unit for storing image formable region information. The transferring apparatus includes: an obtaining unit for obtaining the stored image formable region information; a determination unit for determining an image formation size based on the obtained image formable region information; a unit for expanding or contracting the received medical image data according to the determined image formation size; and a transfer unit for transferring the expanded or contracted image data to the medical image forming apparatus.

7 Claims, 15 Drawing Sheets

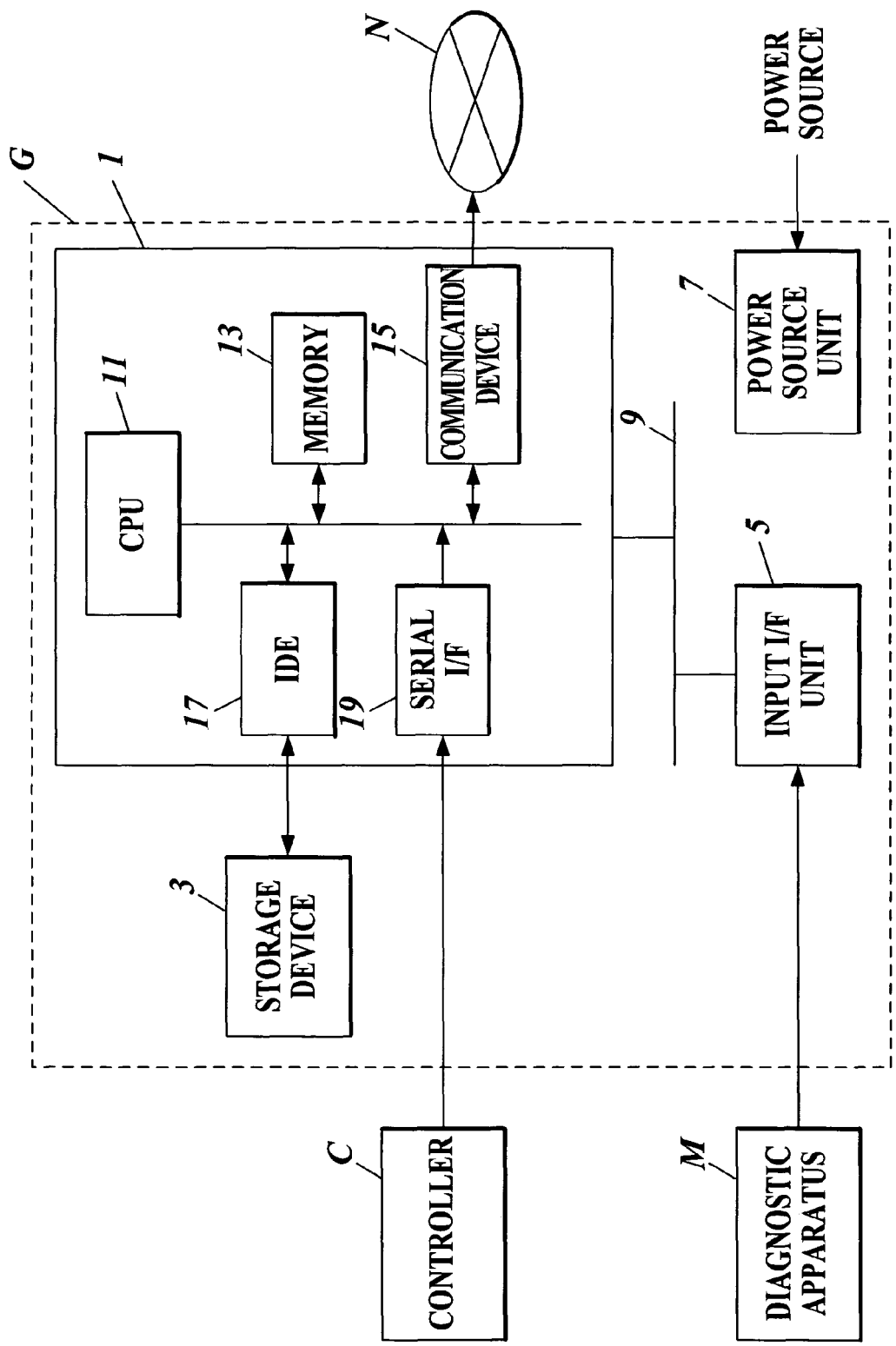

FIG.6

| | MAXIMUM OUTPUT SIZE (mm) | | ONE-PIXEL SIZE (mm) |
|---|---|---|---|
| | VERTICAL SIDE | HORIZONTAL SIDE | |
| FILM OUTPUT APPARATUS F1 | 355 | 540 | $3 \times 10^{-2}$ |
| FILM OUTPUT APPARATUS F2 | 355 | 432 | $4 \times 10^{-2}$ |
| FILM OUTPUT APPARATUS F3 | 497 | 432 | $4 \times 10^{-2}$ |

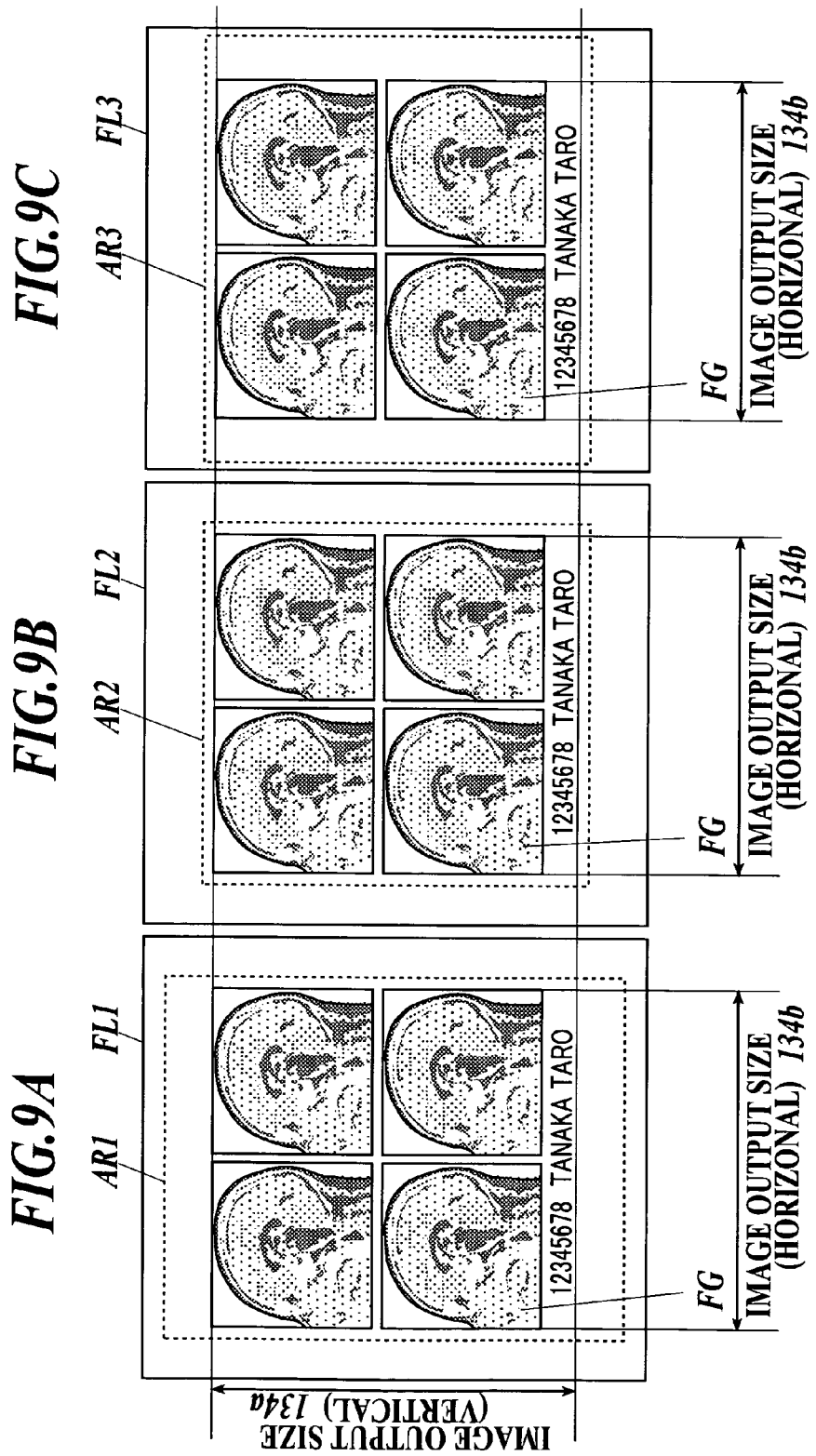

TRANSMITTED IMAGE SIZE

RECEIVED IMAGE SIZE

ONE-FRAME IMAGE REGION SIZE

| FILM SIZE | | MAXIMUM OUTPUT SIZE (mm) | | ONE-PIXEL SIZE (mm) |
|---|---|---|---|---|
| | | VERTICAL SIDE | HORIZONTAL SIDE | |
| FILM OUTPUT APPARATUS F1 | B4 | 355 | 540 | $3 \times 10^{-2}$ |
| | A3 | 400 | 600 | |
| FILM OUTPUT APPARATUS F2 | B4 | 355 | 432 | $4 \times 10^{-2}$ |
| | A3 | 400 | 500 | |
| FILM OUTPUT APPARATUS F3 | B4 | 497 | 432 | $4 \times 10^{-2}$ |
| | A3 | 550 | 500 | |

MEDICAL IMAGE OUTPUT SYSTEM, MEDICAL IMAGE TRANSFERRING APPARATUS AND PROGRAM

BACKGROUND OF THE INVENTION

1. Field of the Invention

The present invention relates to a medical image output system provided with a medical image transferring apparatus transferring received medical image data and a plurality of medical image forming apparatus each outputting a sheet-like recording medium having an image formable region in which the image formation of the medical image based on the transferred medical image data is performed, and the like.

2. Related Art

There has been conventionally known a medical image output system outputting a medical image formed (drawn) on a sheet-like recording medium such as a film, recording paper or the like. The medical image is one having been produced by radiography with various medical image generating apparatus (hereinafter referred to as "diagnostic apparatus") of calculated tomography (CT), calculated radiography (CR), magnetic resonance imaging (MRI), a mammography apparatus, an ultrasonic diagnostic apparatus and the like.

The medical image output system is composed of a diagnostic apparatus, a medical image transferring apparatus (hereinafter referred to a "conversion apparatus") transferring the data of a medical image (hereinafter referred to as "medical image data") generated by the diagnostic apparatus after converting the medical image data into data in accordance with Digital Imaging and Communications in Medicine (DICOM) Standards, and medical image forming apparatus (hereinafter referred to as "output apparatus") each creating a hard copy of the transferred medical image data.

FIG. 14 shows an example of a medical image which has been produced by the radiography of a diagnostic apparatus. As shown in the figure, a medical image FG100 therein includes patient information FG104 besides a radiography image FG102, which has been produced by radiographing a human body. A diagnostic apparatus produces a medical image by synthesizing patient information such as the ID number, the full name and the like of a patient, which have been input by a user, and a radiography image.

FIG. 15A shows an example of a film on which medical images have been formed by a film output apparatus, which is a kind of output apparatus. As shown in the figure, on the film FL100, the medical images FG100, which have been produced by the radiography with the diagnostic apparatus, and patient information FG100 included in the medical images are drawn to be formatted.

As a technique pertaining to the patient information, there has been known a method of performing image formation at a previously specified position and a previously specified size on a film to enable to easily sight the mixing of a film of another patient when a plurality of films are superposed on one another to be subjected to transmission (see JP-2004-226702A; hereinafter referred to as "Patent Document 1").

Now, a region in which an output apparatus can form an image on a sheet-like recording medium (the region is hereinafter referred to as an "image formable region") changes dependently on the version, the series and the like of the output apparatus. For example, in the film FL100 in which a certain output apparatus has performed image formation, the medical image FG100 and the patient information FG100 are drawn in an image formable region AR100 as shown in FIG. 15A. On the other hand, another output apparatus performs image formation in an image formable region AR200 on a film FL200 in FIG. 15B, or a further output apparatus performs image formation in an image formable region AR300 on a film FL300 in FIG. 15C.

In such a manner, the output apparatus expands or contracts a medical image according to severally different image formable region. Consequently, the size of a medical image which has formed on a recording medium may change dependently on an output apparatus. For example, when a doctor performs a diagnosis using recording media severally output from a plurality of output apparatus, a diagnostic mistake may be caused from the difference in each size of the medical image of each recording medium.

Moreover, similarly patient information is also expanded or contracted as well as a medical image according to the image formable region of each output apparatus. Consequently, the size of a character may change dependently on an output apparatus. Hence, even if recording media are superposed on one another as disclosed in Patent Document 1, a character of each recording medium is shifted from one another, and it is difficult to confirm the mixing of a film of another patient.

SUMMARY OF THE INVENTION

The present invention has been made in view of the problems described above, and it is an object of the present invention to realize a medical image output system and the like capable of performing the image formation of a medical image on sheet-like recording media with a plurality of medical image forming apparatus to be the same size.

In order to solve the above-described problem, in accordance with a first aspect of the invention, the medical image output system comprises a medical image transferring apparatus transferring received medical image data, and a plurality of medical image forming apparatus each outputting a sheet-like recording medium having an image formable region in which image formation of a medical image based on the transferred medical image data is performed, wherein each of the medical image forming apparatus includes a storage unit for storing image formable region information representing the image formable region; and the medical image transferring apparatus includes: an obtaining unit for obtaining the image formable region information stored in the storage unit of each of the plurality of medical image forming apparatus; a determination unit for determining an image formation size based on the image formable region information obtained by the obtaining unit; an expansion or contraction unit for expanding or contracting the received medical image data according to the image formation size determined by the determination unit; and a transfer unit for transferring the medical image data expanded or contracted by the expansion or contraction unit to the medical image forming apparatus.

According to the first aspect of the present invention, the image formable region information is obtained from each of the plurality of medical image forming apparatus, and the medical image is expanded or contracted according to the image formation size determined based on the obtained image formable region information. After that, the medical image data is transferred to the medical image forming apparatus. Consequently, the size of the medical image of the image formation on the sheet-like recording medium by the medical image forming apparatus becomes the size according to the image formation size. Thus, even if the image formable region changes dependently of the plurality of medical image forming apparatus, the medical images having the same sizes according to the image forming size can be subjected to the image formation on the sheet-like recording medium to be outputted.

In accordance with a second aspect of the invention, the medical image output system, comprising a medical image transferring apparatus transferring received medical image data, and a plurality of medical image forming apparatus each outputting a sheet-like recording medium having an image formable region in which image formation of a medical image based on the transferred medical image data is performed, wherein each of the medical image forming apparatus includes a storage unit for storing image formable region information representing the image formable region; and the medical image transferring apparatus includes: an obtaining unit for obtaining the image formable region information stored in the storage unit of each of the plurality of medical image forming apparatus; a determination unit for determining an image formation size based on the image formable region information obtained by the obtaining unit; and a transmission unit for transmitting the image formation size determined by the determination unit to each of the medical image forming apparatus, wherein each of the medical image forming apparatus includes: a receiving unit for receiving the image formation size transmitted from the transmission unit; an expansion or contraction unit for expanding or contracting the transferred medical image data according to the image formation size received by the receiving unit; and an image formation unit for performing image formation of the medical image data expanded or contracted by the expansion or contraction unit on the sheet-like recording medium.

According to the second aspect of the invention, the medical image transferring apparatus obtains the image formable region information from each of the plurality of medical image forming apparatus, and determines the image formation size based on the obtained image formable region information. On the other hand, after the medical image forming apparatus has expanded or contracted the medical image data according to the image formation size transmitted from the medical image transferring apparatus, the medical image forming apparatus performs the image formation of the medical image based on the medical image data. Consequently, the size of the medical image the image formation of which the medical image forming apparatus performs on the sheet-like recording medium becomes the size according to the image formation size. Consequently, even if the image formable region changes dependently on the plurality of medical image forming apparatus, the medical images having the same sizes according to the image formation size can be subjected to the image formation on the sheet-like recording medium to be outputted.

Moreover, when the medical image forming apparatus expands the medical image data to perform the image formation, the medical image data which the medical image transferring apparatus transfers to the medical image forming apparatus is the data before the expansion. Consequently, the communication capacity of the data between the medical image transferring apparatus and the medical image forming apparatus can be reduced.

Preferably, the determination unit determines an image formation size falling into all of the image formable regions of the plurality of medical image forming apparatus based on the image formable region information obtained by the obtaining unit.

According to such a configuration, the image formation size is determined so that the image formation size may fall into the whole image formable region of the plurality of medical image forming apparatus. Consequently, the medical image the image formation of which the medical image forming apparatus performs surely receives the image formation in the image formable region of each of the medical image forming apparatus.

Preferably, the image formable region information includes lengths of a vertical side and a horizontal side of the image formable region, and the image formation size determination unit selects a minimum vertical side length and a minimum horizontal side length among each of the image formable region information of the plurality of medical image forming apparatus obtained by an obtaining unit, and determines the selected lengths as an image output size.

According to such s configuration, the minimum vertical side and the minimum horizontal side among the vertical sides and the horizontal sides of the image formable region information are selected, and are determined as the image output size.

Preferably, the medical image data includes a radiography image produced by radiographing a subject, and patient information.

Accordingly, the medical image data includes the radiography image produced by radiographing the subject and the patient information. Consequently, because the radiography images and the patient information are drawn on the sheet-like recording media output by the plurality of medical image forming apparatus, when the plurality of sheet-like recording media is transmitted in the sate of being superposed on one another, each of the radiography images and the patient information is in the same size, and do not produce any shifts. Consequently, for example, whether the sheet-like recording medium of another patient is mixed among the plurality of sheet-like recording media output from different medical image forming apparatus or not can be easily confirmed by superposing the sheet-like recording media on one another.

In accordance with a third aspect of the invention, the medical image transfer apparatus receiving medical image data to transfer the received medical image data to a plurality of medical image forming apparatus, comprising: an obtaining unit for obtaining image formable region information from each of the plurality of medical image forming apparatus; a determination unit for determining an image formation size based on the image formable region information obtained by the obtaining unit; an expansion or contraction unit for expanding or contracting the received medical image data according to the image formation size determined by the determination unit; and a transfer unit for transferring the medical image data expanded or contracted by the expansion or contraction unit to the medical image forming apparatus.

According to such an aspect of the invention, the image formable region information is obtained from each of a plurality of medical image forming apparatus, and the medical image data is expanded or contracted according to the image formation size determined based on the obtained image formable region information. After that, the medical image data is transferred to the medical image forming apparatus. Consequently, the size of the medical image the image formation of which the medical image forming apparatus performs on the sheet-like recording medium is the size according to the image formable size. Consequently, even when the image formable regions of the plurality of medical image forming apparatus differ from one another, the medical images having the same sizes according to the image formation size can be subjected to the image formation on the sheet-like recording medium to be output.

In accordance with a fourth aspect of the invention, the program for making a computer realize a function of receiving medical image data to transfer the received medical image data to a plurality of medical image forming apparatus, the program comprising: an obtaining function of obtaining image formable region information from each of the plurality of medical image forming apparatus; a determining function of determining an image formation size based on the image formable region information obtained by the obtaining function; an expansion or contraction function of expanding or contracting the received medical image data according to the image formation size determined by the determining function; and a transfer function of transferring the medical image data expanded or contracted by the expansion or contraction function to the medical image forming apparatus.

According to such a program, the image formable region information is obtained from each of a plurality of medical image forming apparatus, and the medical image data is expanded or contracted according to the image formation size determined based on the obtained image formable region information. After that, the medical image data is transferred to the medical image forming apparatus. Consequently, the size of the medical image the image formation of which the medical image forming apparatus performs on the sheet-like recording medium is the size according to the image formable size. Consequently, even when the image formable regions of the plurality of medical image forming apparatus differ from one another, the medical images having the same sizes according to the image formation size can be subjected to the image formation on the sheet-like recording medium to be output.

BRIEF DESCRIPTION OF THE DRAWINGS

The present invention will become more fully understood from the detailed description given hereinafter and the accompanying drawings which are given by way of illustration only, and thus are not intended as a definition of the limits of the present invention, and wherein:

FIG. 4 is a diagram showing an example of the functional configuration of a conversion apparatus;

FIG. 6 is a diagram showing an example of the table configuration of an output apparatus setting information table;

FIGS. 9A, 9B and 9C are figures showing examples of general views of films which respective film output apparatus have output;

FIG. 13 is a diagram showing an example of the table configuration of an output apparatus setting information table in a modification example;

DETAILED DESCRIPTION OF THE PREFERRED EMBODIMENTS

First, a first embodiment of a medical image output system in the case where a medical image transferring apparatus according to the present invention is composed of a conversion apparatus and a controller and a medical image forming apparatus is applied to a film output apparatus is described in detail by referring to FIGS. 1-9.

Figure 1:
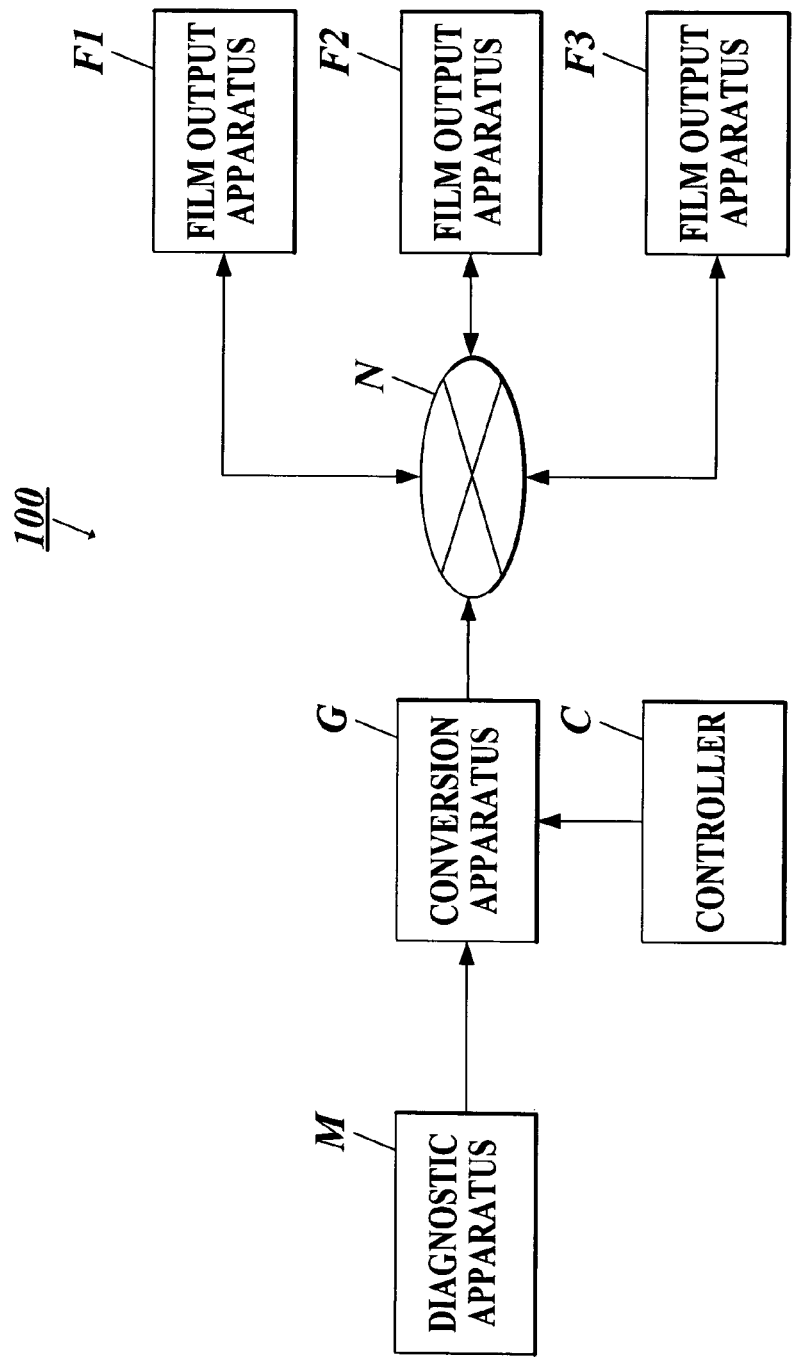
FIG. 1 is a diagram showing an example of the system configuration of a medical image output system to which the present invention is applied.

FIG. 1 is a diagram showing an example of the system configuration of a medical image output system 100. According to the diagram, the medical image output system 100 is composed of a conversion apparatus G transferring a medical image output from a diagnostic apparatus M in conformity with an instruction of a controller C, and film output apparatus F1, F2 and F3, which are connected to one another through a predetermined communication network N.

A user determines whether to perform the film output of the data of a medical image (hereinafter referred to as "medical image data") generated by the radiography with the diagnostic apparatus M or not by using the controller C. The controller C is made to perform the display output of the imaging image of each page of a film on a display unit.

When the user sets and settles an arrangement method of frames of medical images by operating the controller C and specifies a film output apparatus from which a film is made to be output, the conversion apparatus G formats the medical image data, and transfers the formatted medical image data to the specified film output apparatus through the communication network. Each of the film output apparatus F1, F2 and F3 performs the image formation of an image based on the medical image data transmitted from the conversion apparatus G on a film, and outputs the image.

The diagnostic apparatus M is a medical image generating apparatus radiographing a subject to generate medical image data (an analog or digital video signal). The diagnostic apparatus M is composed of a control unit, a radiographing unit, a display unit, an input unit, an I/F unit and the like. The control unit synthesizes a radiography image radiographed with the radiographing unit, and patient information such as an ID number, a full name, sex, an age and the like which have been input from the input unit to generate medical image data. Then, the control unit transmits the generated medical image data to the conversion apparatus G.

As the diagnosis apparatus M, a CR and a CT, which irradiates an X-ray to perform radiography and reads an X-ray image stored in a photostimulable phosphor plate by the radiography to genera digital data, or an MRI, an ultrasonic photographing apparatus and the like without being limited to the sue of the X-ray, can be suitably applied.

The film output apparatus F1 is a medical image forming apparatus performing the image formation of an image on a film based on data in conformity with DICOM Standards transferred from the conversion apparatus G, and outputs the formed image. The film output apparatus F1 is composed of a control unit, an image memory, an exposure unit, a development unit, a communication unit, an ejection unit and the like. A film, which is a sheet-like recording medium, is one composed of a supporting body and an emulsion coated on the supporting body to form a photosensitive layer. The supporting body is made of polyethylene terephthalate (PET) or the like, and the emulsion contains a photosensitive material having photosensitive and thermosensitive properties.

The film is conveyed to each configuration unit by a conveyance unit in conformity with the control of the control unit. The exposure unit radiates a laser beam onto the film to perform exposure, and forms a latent image of an image based on the data transferred from the conversion apparatus G. The development unit heats the film after the exposure to visualize (develop) the latent image formed by the exposure. And the film developed and ejected is ejected from the ejection unit. Incidentally, although the medical image forming apparatus is applied to the film output apparatus, the medical image forming apparatus may be applied to various image forming apparatus such as a laser printer, an inkjet printer and the like. Incidentally, because the basic configurations of the film output apparatus F2 and F3 are the same as that of the film output apparatus F1 described above, their descriptions are omitted.

Figure 2:
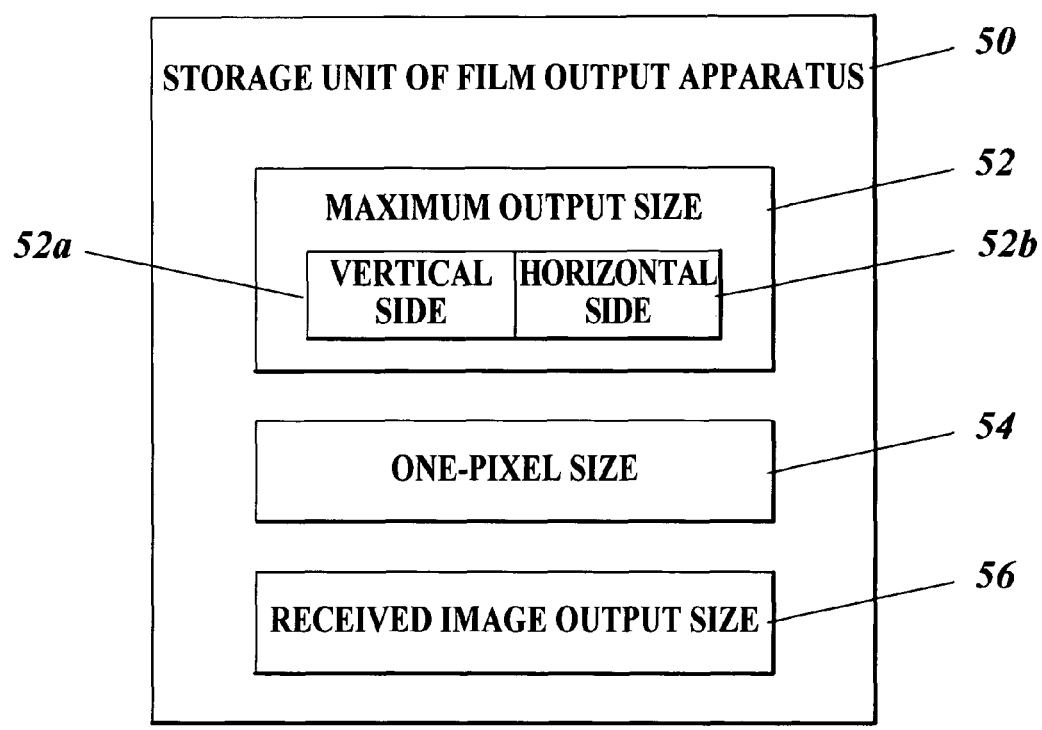
FIG. 2 is a diagram showing an example of the data configuration of the storage unit of a film output apparatus according to a first embodiment.

The control unit of the film output apparatus F1 is composed of a CPU, a storage unit 50, which is a storage unit, and the like, and FIG. 2 shows an example of the data configuration of the storage unit 50. According to the diagram, the storage unit 50 stores a maximum output size 52, a one-pixel size 54 and a received image output size 56.

The maximum output size 52 is the information representing the maximum region (image formable region) in which the film output apparatus F1 can form an image on the film, i.e. image formable region information, and is indicated by the number of the pixels on a vertical side 52$a$ and a horizontal side 52$b$. The one-pixel size 54 is the size of one dot when the film output apparatus F1 performs image formation.

The maximum output size 52 and the one-pixel size 54 are initial information set in the film output apparatus F1, F2 and F3 peculiarly, and changes pursuant to versions, the series of products, and the like.

The received image output size 56 is an image output size 134 transmitted from the conversion apparatus G. In DICOM Standards preexists a function of performing image formation by expanding or contracting of an image to the size of one side or two sides (mm) of the image to be subjected to the image formation when the sizes are specified. The film output apparatus F performs the image formation by expanding or contracting the image based on received template data in accordance with the received image output size 56.

Figure 3A:
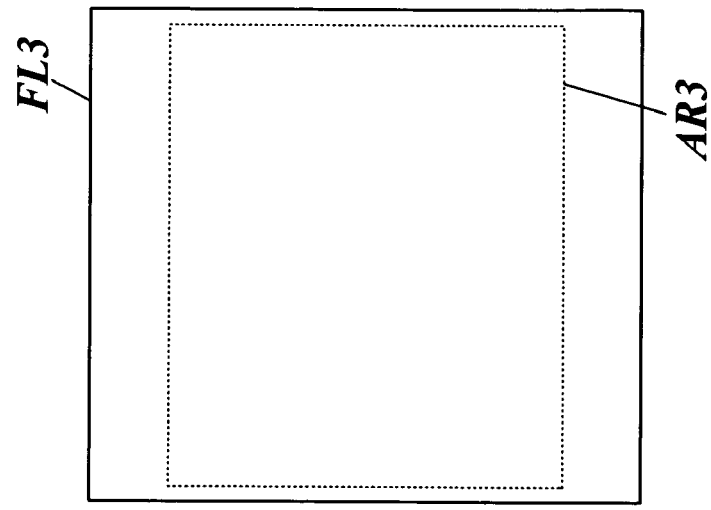
FIGS. 3A, 3B and 3C are diagrams for illustrating the image formable region of each film output apparatus.
Figure 3B:
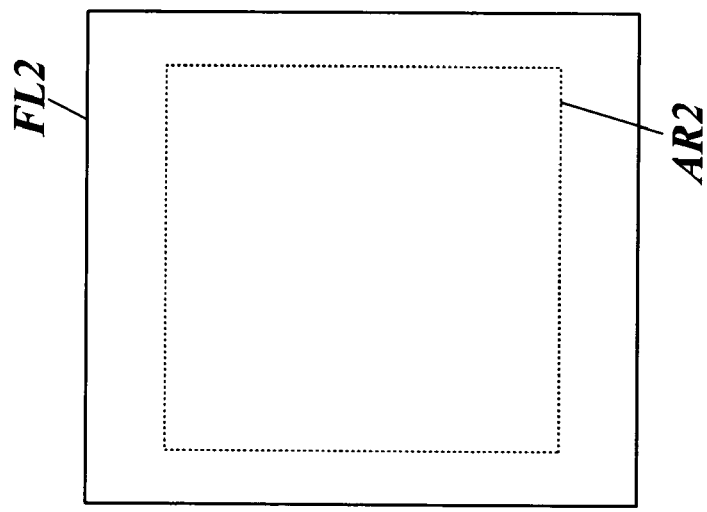
Figure 3C:
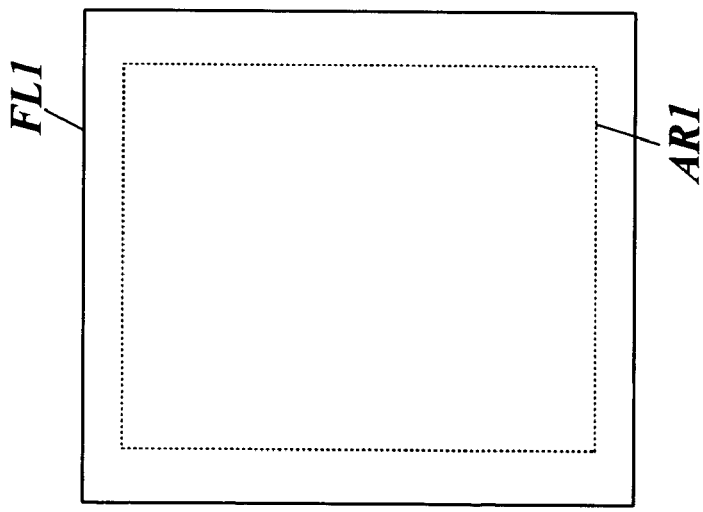

FIGS. 3A, 3B and 3C are diagrams representing the image formable regions of the film output apparatus F1, F2 and F3, respectively. Incidentally, it is supposed that the sizes of films FL1-FL3 shown in the diagram are severally the same size.

The film output apparatus F1, F2 and F3 perform image formation into image formable regions AR1, AR2 and AR3 of films FL1, FL2 and FL3 in FIGS. 3A, 3B and 3C, respectively. In such a manner, the image formable regions change dependently on the film output apparatus.

The controller C is a functional unit equivalent to, so to speak, the user interface of the conversion apparatus G, which performs the arrangement setup of a frame of a medical image, the specification of the film output apparatus which is made to output a medical image, and the like. The controller C is composed of a CPU, a storage device, a display unit, an input unit, an I/F unit and the like.

The CPU of the controller C makes the display unit display a predetermined input form, and sets format information in a RAM in conformity with a user's operation of an input unit. The format information is the setting information of an arrangement method of medical images pertaining to how to arrange the frames of the medical images on one film, the font and the character size of patient information, and the like.

The input form of format information may be one for allowing a user to input the arrangement method of medical images in a numerical form of "the horizontal number of frames×the number of vertical frames", such as "2×2" and "3×3", or may be one for allowing a user to input the arrangement graphically by allowing the user to move a predetermined icon representing an medical image.

And the CPU makes the display unit display a selection screen of the film output apparatus after the setting of the format information, and allows the user to specify an image transmission destination of the medical image. The image transmission destination is an identifier representing any of the film output apparatus F1, F2 and F3 to which the conversion apparatus G transmits medical image data to make the apparatus perform image formation. The CPU transmits these set and specified format information and image transmission destination to the conversion apparatus G. Incidentally, although the present embodiment is configured so that the format information and an image output destination are set by the controller C, the embodiment may be also configured to be able to perform the setting of them with the diagnostic apparatus M, for example.

The conversion apparatus G reads medical image data output from the diagnostic apparatus M one piece of data at a time, and performs the data conversion of the read medical image data in conformity with DICOM Standards to store the converted medical image data. After that, the conversion apparatus G transfers the stored medical image data to the specified film output apparatus.

FIG. 4 is a block diagram showing an example of the functional configuration of the conversion apparatus G. According to the diagram, the conversion apparatus G is composed of a control unit 1, a storage device 3, an input I/F unit 5 and a power source unit 7, all connected to a bus 9.

The storage device 3 is a functional unit equipped with a storage medium performing the reading and the writing of data optically or magnetically. The storage device 3 is composed of, for example, a hard disk drive (HDD) or the like.

The input I/F unit 5 is a functional unit receiving the medical image data transmitted from the diagnostic apparatus M. The input I/F unit 5 is composed of, for example, a serial interface such as RS232C, a parallel interface such as Centronics, USB and the like. The power source unit 7 supplies electric power to each unit of the conversion apparatus G.

The control unit 1 performs the overall management and control of the conversion apparatus G such as the management and control of data processing, data communication and the like. The control unit 1 is composed of a CPU 11, a memory 13, a communication device 15, an IDE 17 and a serial interface 19.

The CPU 11 reads a program stored in the storage device 3, and performs the processing in conformity with the program. More specifically, the CPU 11 receives the format information and the image transmission destination, which have been transmitted from the controller C, through the serial interface 19, and obtains the medical image data stored in the storage device 3 through the IDE 17. Subsequently, the CPU 11 produces template data using these pieces of data, and then the CPU 11 transfers the produced template to a film output apparatus through the communication device 15.

The memory 13 is a storage region temporarily holding the various programs which CPU 11 performs, the data pertaining to the execution of these programs, and the like.

Figure 5A:
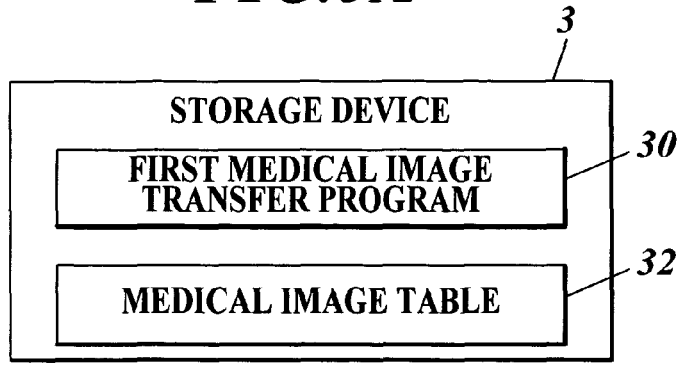
FIG. 5A is a diagram showing an example of the data configuration of the storage device of a conversion apparatus in the first embodiment.

FIG. 5A is a diagram showing an example of the data configuration of the storage device 3. According to the diagram, the storage device 3 stores a first medical image transfer program 30 and a medical image table 32.

The medical image transfer program 30 is a program for realizing a first medical image transfer processing (see FIG. 8) pertaining to the first embodiment. The medical image table 32 is a data table in which medical image data transmitted from the diagnostic apparatus M are accumulatively stored.

Figure 5B:
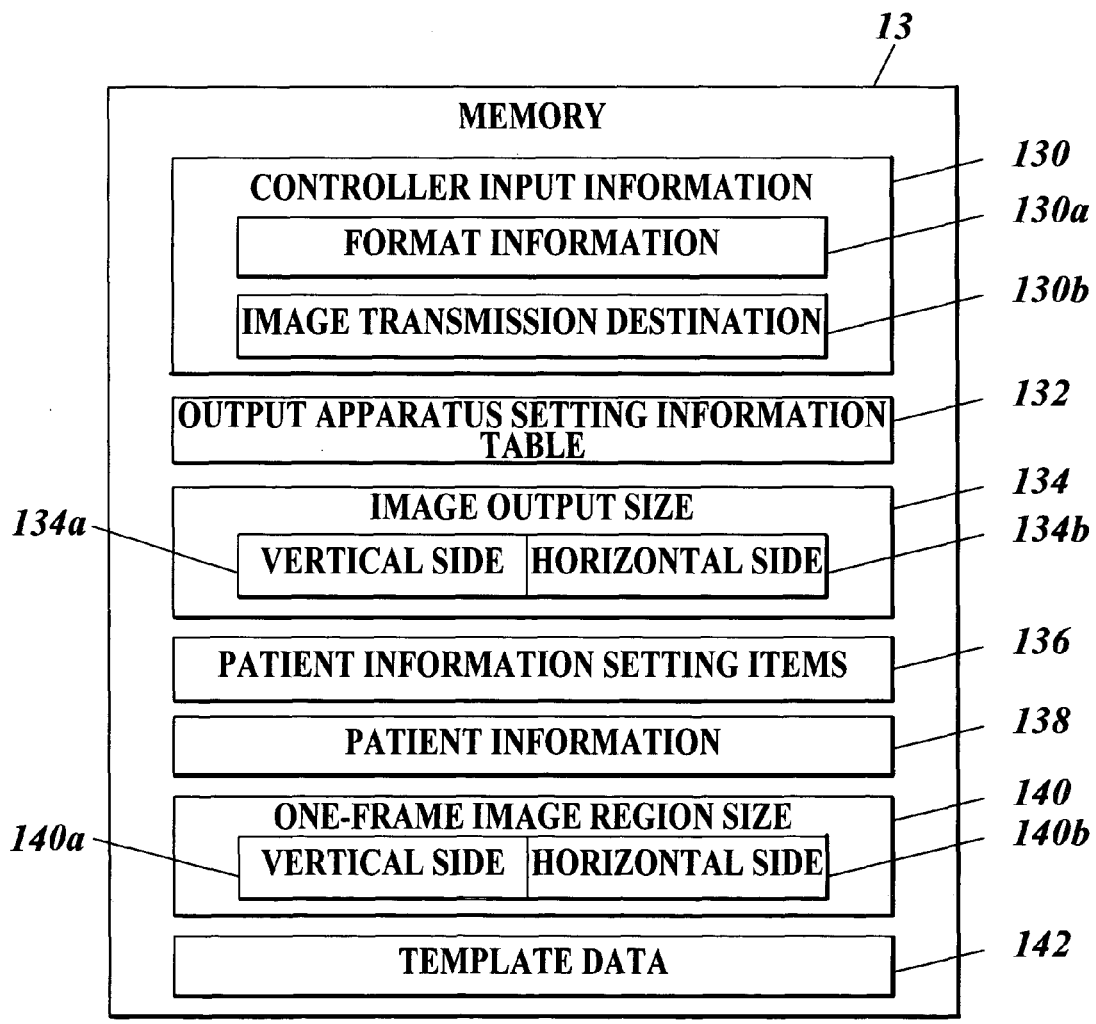
FIG. 5B is a diagram showing an example of the data configuration of a memory of the conversion apparatus.

FIG. 5B is a diagram showing an example of the data configuration of the memory 13. According to the diagram, the memory 13 stores controller input information 130, an output apparatus setting information table 132, the image output size 134, patient information setting items 136, patient information 138, a one-frame image region size 140 and template data 142.

The controller input information 130 is composed of format information 130a and an image transmission destination 130b. The CPU 11 obtains the format information and the image transmission destination which have been input by the user using the controller C through the serial I/F 19 to store the obtained format information and the image transmission destination in the memory 13.

The output apparatus setting information table 132 is a data table storing the maximum output size 132-1 and a one-pixel size 132-2 of each film output apparatus correspondingly as shown in FIG. 6 as an example of the data configuration. The CPU 11, which realizes an obtaining unit, communicates with each of the film output apparatus F1, F2 and F3 through the communication device 15, and obtains the maximum output size and the one-pixel size from each apparatus, to correspondingly store them in the output apparatus setting information table 132.

For example, the maximum output size corresponding to the film output apparatus F1 is represented by the lengths of a vertical side and the horizontal side of the image formable region AR1 shown in FIG. 3A. Similarly, the image formable regions AR2 and AR3 of the film output apparatus F2 and F3 are represented by the vertical sides and the horizontal sides of FIGS. 3B and 3C, respectively.

The CPU 11, which realizes a determination unit, determines the image output size 134 (image formation size) using the maximum output size 132-1 stored in the output apparatus setting information table 132. The image output size 134 is the size of the region in which a film output apparatus performs image formation, and is represented by the numbers of pixels of a vertical side 134a and a horizontal side 134b. The CPU 11 selects the minimum vertical side and the minimum horizontal side among the vertical sides and the horizontal sides of the maximum output size 132-1 stored in the output apparatus setting information table 132, respectively, and determines them as the image output size 134. Consequently, the image output size 134 becomes a size falling into the image formable region of any of the film output apparatus F1-F3.

The patient information setting items 136 are the setting information pertaining to the drawing of patient information such as the kind of the item of the patient information which is drawn on a film, the drawing order, the number of character lines, and the like. The CPU 11 determines, for example, the output order of the items of patient information such as an ID number and a full name, and the number of lines at the time of starting a new line according to the horizontal side 134b of the image output size 134 as the patient information setting items 136. Incidentally, the patient information setting items 136 may be set by a user using the controller C to be transferred together with format information and the like.

The patient information 138 is patient information included in the medical image data stored in the medical image table 32, and character recognitions is obtained by an OCR, pattern recognition, and the like. Incidentally, the obtaining method of the patient information 138 may be one, for example, obtaining an ID number from medical image data, and referring for the ID number to the server on Hospital Information System (HIS) or Radiology Information System (RIS) to obtain the items of the other patient information from the server.

The one-frame image region size 140 is the size of the region in which image formation of one frame of a medical image based on medical image data is performed on a film, and is represented by the numbers of pixels of a vertical side 140a and a horizontal side 140b. Here, a calculation method of the one-frame image region size 140 is simply described, referring to the diagram of FIG. 7 expressing the template data 142. The description becomes like the following one.

First, the one-pixel size 132-2 corresponding to the film output apparatus represented by the image transmission destination 130b of the controller input information 130 is selected from the output apparatus setting information table 132. And an image space SP of the numbers of pixels, a trim width W, a character size CS (vertical) and a character drawing region AR20 are calculated using formulae (1)-(5) using the selected one-pixel size. Incidentally, it is supposed that the actual size vales (lengths) of the image space, the trim width, the character size and the number of character lines are given by user's initial setting.

$$\text{Image Space } SP = \text{Image Space [actual size value]} \div \text{One-Pixel Size} \quad (1)$$

$$\text{Trim Width } W = \text{Trim Width [actual size value]} \div \text{One-Pixel Size} \quad (2)$$

$$\text{Character Size } CS \text{ (vertical)} = \text{Character Size [actual size value]} \div \text{One-Pixel Size} \quad (3)$$

$$\text{Character Drawing Region } AR20 \text{ (horizontal)} = \text{Image Output Size (horizontal) } 134b \text{ [number of pixels]} \quad (4)$$

$$\text{Character Drawing Region } AR20 \text{ (vertical)} = \text{Character Size } CS \text{ (vertical) [number of pixels]} \times \text{Number of Character Lines} \quad (5)$$

And the image drawing region AR10, which is a region in which medical images are drawn, is calculated using formulae (6) and (7).

$$\text{Image Drawing Region } AR10 \text{ (horizontal)} = \text{Image Output Size (horizontal) } 134b - ((\text{Trim Width } W \times 2 \times \text{Horizontal Number of Frames}) + (\text{Image Space } Sp \times (\text{Horizontal Number of Frames} - 1))) \quad (6)$$

$$\text{Image Drawing Region } AR10 \text{ (vertical)} = \text{Image Output Size (vertical) } 134a - (\text{Trim Width } W \times 2 \times \text{Vertical Number of Frames}) + (\text{Image Space } Sp \times (\text{Vertical Number of Frames} - 1)) - \text{Character Drawing Region } AR20 \text{ (vertical)} \quad (7)$$

The CPU 11 calculates one-frame image region size 140 using formulae (8) and (9) after calculating the image drawing region AR10 and the character drawing region AR20.

$$\text{One-Frame Image Region Size (vertical) } 140a = \text{Image Drawing Region } AR10 \text{ (vertical)} \div \text{Vertical Number of Frames} \quad (8)$$

One-Frame Image Region Size (horizontal) $140b$=
Image Drawing Region $AR10$ (horizontal)÷Horizontal Number of Frames  (9)

The template data 142 is image data which is generated by formatting and synthesizing medical image data and the image data of the patient information 138. The CPU 11 calculates one-frame image region size 140 before performing image processing of expanding or contracting the medical image data stored in the medical image table 32 according to the one-frame image region size 140. And the CPU 11 converts the character data of the patient information 138 into the image data of the font and the character size in accordance with the format information 130a.

Figure 7:
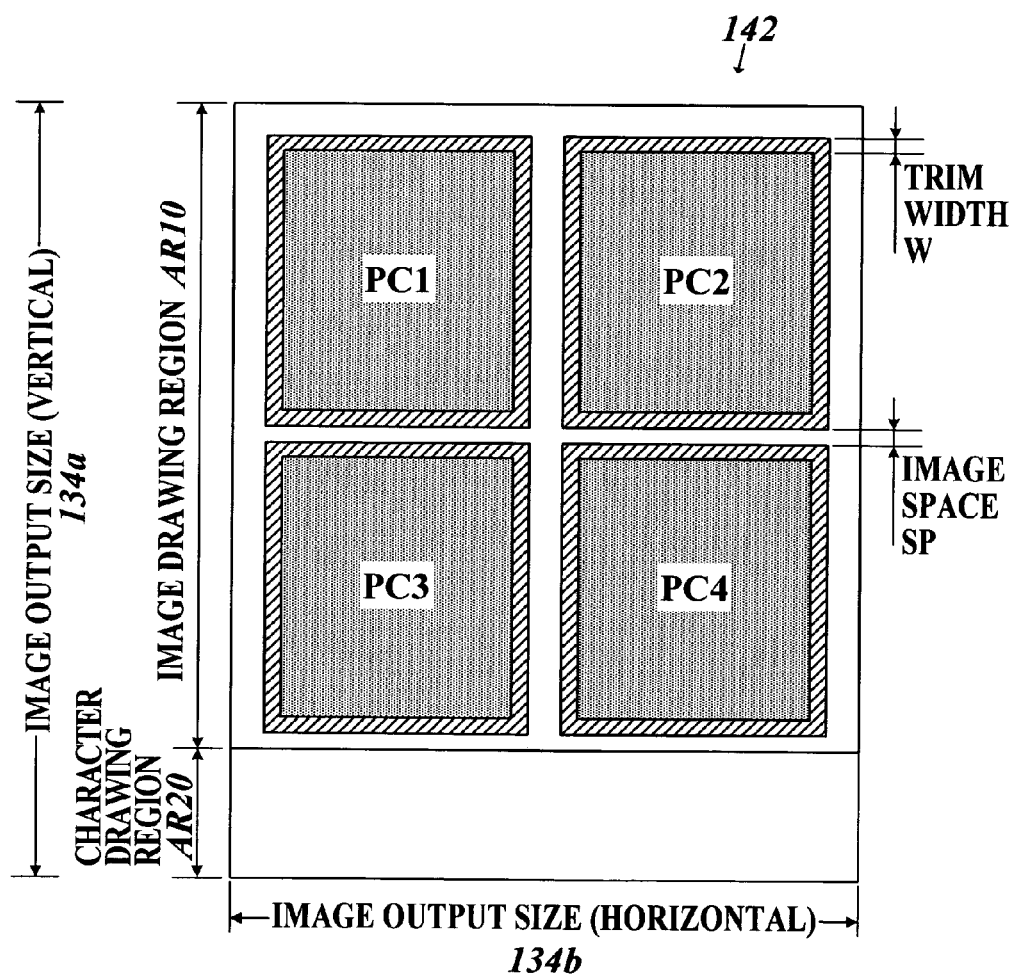
FIG. 7 is a diagram for illustrating template data.

The CPU 11 embeds and arranges the medical image data after the expansion or the contraction into the image drawing region AR10, and embeds and arranges the patient information of image data into the character drawing region AR20, and generates the template data 142 as shown in FIG. 7 with the image data in conformity with DICOM Standards. Consequently, the template data 142 is generated in the size of the vertical side $134a$×the horizontal side $134b$ of the image output size 134.

Figure 8:
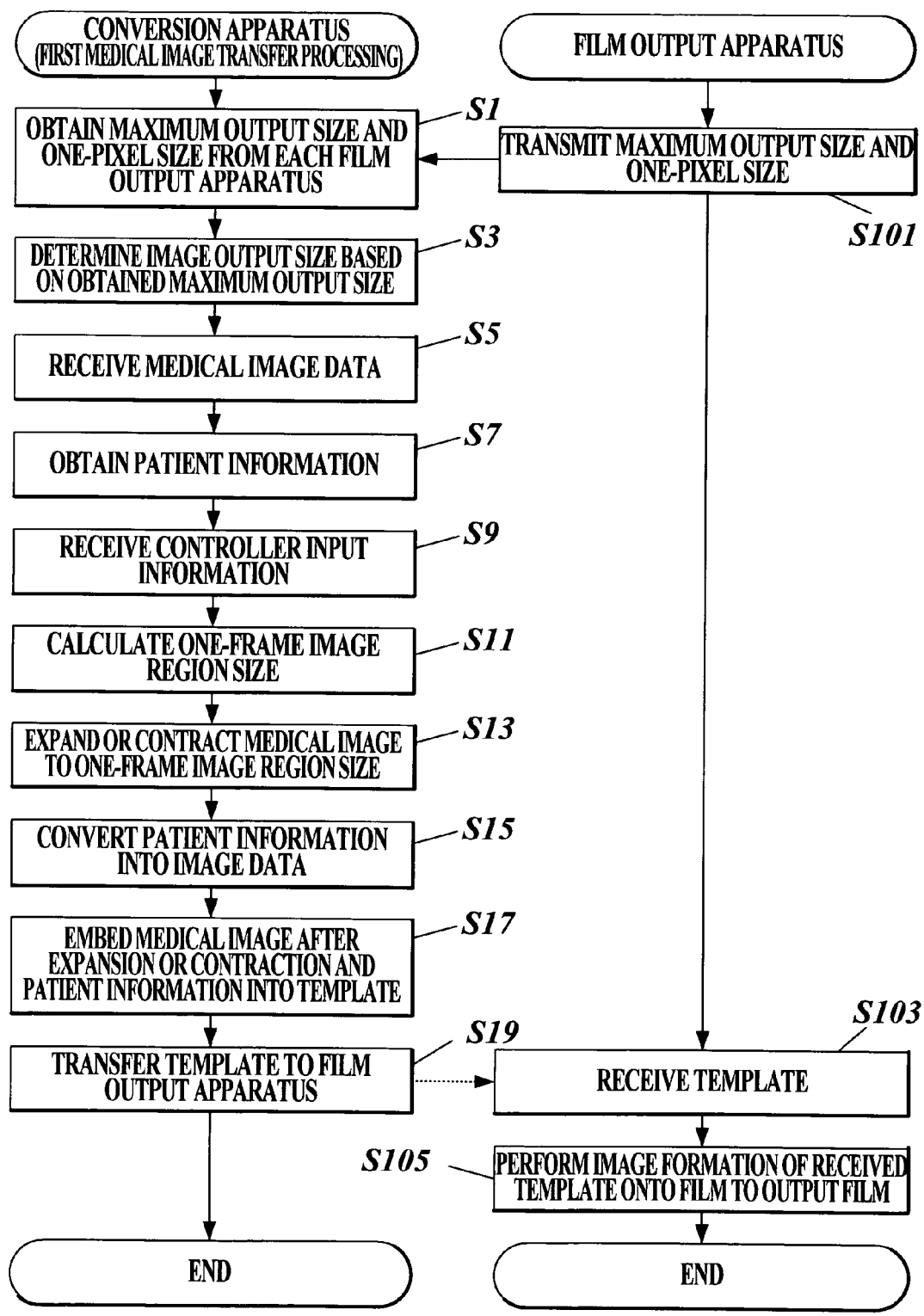
FIG. 8 is a flowchart for illustrating a concrete operation of the medical image output system according to the first embodiment.

Next, the concrete operation of the medical image output system 100 is described using the flowchart of FIG. 8. First, when the CPU 11 of the conversion apparatus G starts the first medical image transfer processing, the CPU 11 obtains the maximum output size and the one-pixel size from each of the film output apparatus F1, F2 and F3, and stores the obtained sizes into the output apparatus setting information table 132 so as to correspond with each film output apparatus (Step S1).

On the film output apparatus side, each film output apparatus transmits each maximum output size 52 and one-pixel size 54 (Step S101).

The CPU 11 determines the image output size 134 based on the maximum output size 132-1 in the output apparatus setting information table 132 (Step S3), and then the CPU 11 receives medical image data transmitted from the diagnostic apparatus M to store and record the received medical image data in the medical image table 32 (Step S5).

The CPU 11 performs the character recognition of the patient information 138 to obtain the information 138 from the medical image data stored in the medical image table 32 (Step S7), and receives format information and an image transmission destination from the controller C to store the received information and destination in the memory 13 as the controller input information 130 (Step S9). Subsequently, the CPU 11 calculates the one-frame image region size 140 according to the calculation method described above (Step S11), and expands or contracts the medical image data in the medical image table 32 according to the one-frame image region size 140 (Step S13). Thereby, an expansion or contraction unit is realized.

The CPU 11 converts the patient information 138 obtained at Step S7 into image data (Step S15), and embeds the patient information after the image conversion and the medical image data after the expansion or the contraction into the template data 142 as shown in FIG. 7 to produce the template data 142 (Step S17). The CPU 11, which realizes a transfer unit, ends the first medical image transfer processing after transferring the template data 142 to the film output apparatus represented by the image transmission destination 130b together with the image output size 56 (Step S19).

On the other hand, the film output apparatus receives the template data and the image output size which are transferred from the conversion apparatus G after the processing at Step S101 (Step S103). And the film output apparatus adjusts the image based on the template data 142 according to the received image output size 56, and performs the image formation thereof in the center of the film to output the image (Step S105). Incidentally, the adjustment of the size of the image may be preformed on the basis of either of the vertical side or the horizontal side of the received image output size 56, or may be performed to adjust the size to both the sides.

FIGS. 9A, 9B and 9C are figures showing examples of the general views of the films output from the film output apparatus F1, F2 and F3, respectively. The film output apparatus F1 outputs the film FL1 of FIG. 9A. Because the template 142 transmitted from the conversion apparatus G has the size determined based on the maximum output size 52 of each film output apparatus so as to be in accordance with the image output size 134, a medical image FG having the size of the image output size 134 is drawn in the center on the film FL1. Moreover, the medical image FG of the size of the image output size 134 is drawn on films FL2 and FL3 (see FIGS. 9B and 9C). As shown in these figures, all the sizes of the respective medical images drawn on the respective films are unified to the same size, and also the size of the patient information becomes the same size.

As described above, according to the first embodiment, the conversion apparatus obtains the maximum output size which each film output apparatus holds, and determines the image output size 134 based on the maximum output size. The image output size is one obtained by selecting the minimum vertical side and the minimum horizontal side of the maximum output size 52 of each film output apparatus. Consequently, each film output apparatus can perform the image formation of a medical image in the size same in the respective image formable regions different from one another. Consequently, because the sizes of the medical images drawn on films are the same irrespective of the versions and the series of the film output apparatus, a comparison diagnosis among films output from different film output apparatus becomes easy. Moreover, a doctor's diagnostic mistake can be prevented in the comparison diagnosis.

Moreover, also the patient information of the image data embedded in the template data 142 is subjected to the image formation on films using the same font and the characters of the same size. Consequently, when films output from different film output apparatus are superposed on one another, if the films are ones radiographing the pieces of patient information of the same patient, the pieces of the patient information are superposed on one another without shifting. Consequently, the mixing of a film of another patient can be easily confirmed.

Next, a second embodiment is described using FIGS. 10-13. Incidentally, in the following description, the same marks are given to the same configurations as those of the medical image output system 100 of the first embodiment described above, and their descriptions are omitted.

Figures 10A, 10B:
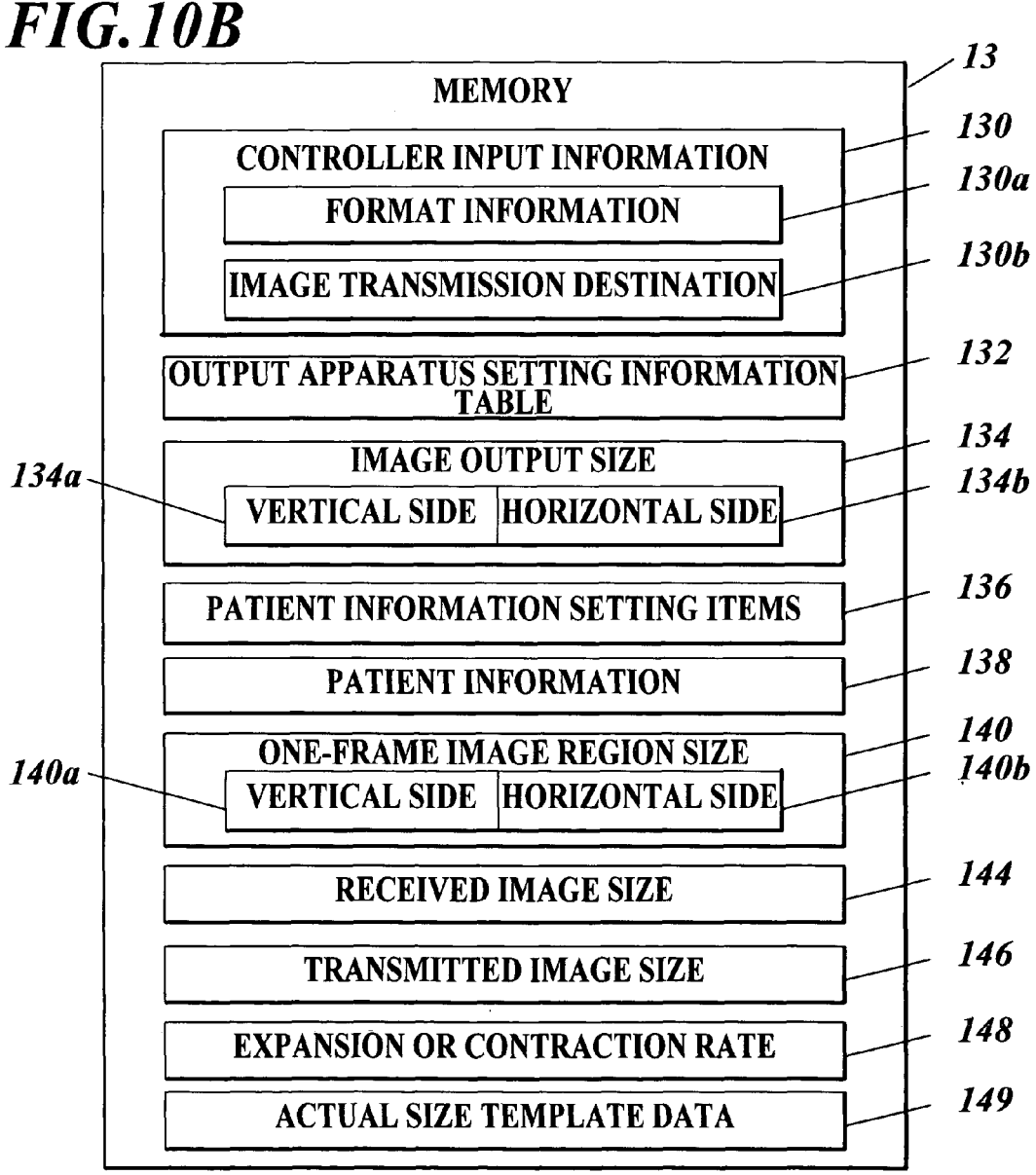
FIG. 10A is a diagram showing an example of the data configuration of a storage device of a conversion apparatus according to a second embodiment.
FIG. 10B is a diagram showing an example of the data configuration of a memory of the conversion apparatus.

FIG. 10A is a diagram showing an example of the data configuration of the storage device 3 in the second embodiment. According to the diagram, the storage device 3 stores a second medical image transfer program 34 and the medical image table 32. The second medical image transfer program 34 is a program for realizing a second medical image transfer processing (see FIG. 13) pertaining to the second embodiment.

FIG. 10B is a diagram showing an example of the data configuration of the memory 13 of the second embodiment. According to the diagram, the memory 13 stores the controller input information 130, the output apparatus setting information table 132, the image output size 134, the patient information setting items 136, the patient information 138, the one-frame image region size 140, a received image size 144, a transmitted image size 146, an expansion or contraction rate 148, and an actual size template data 149.

The received image size 144 is an image size (number of pixels) of medical image data received from the diagnostic apparatus M, i.e. the medical image data stored in the medical image table 32. For example, the CPU 11 obtains the received image size 144 from the header information included in the data at the time of the reception of the medical image data, or calculates the received image size 144 from the data capacity of the data.

Figure 11C:
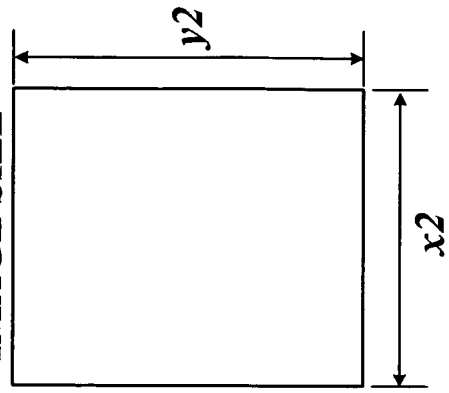
FIGS. 11A, 11B and 11C are diagrams for illustrating a one-frame image region size, a received image size and a transmitted image size, respectively.
Figure 11B:
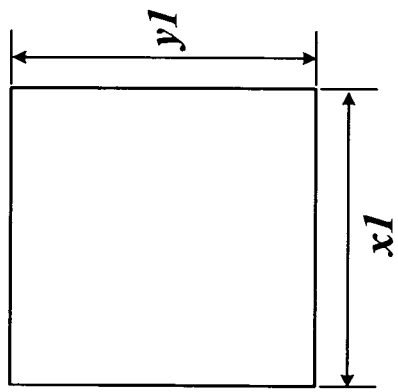
Figure 11A:
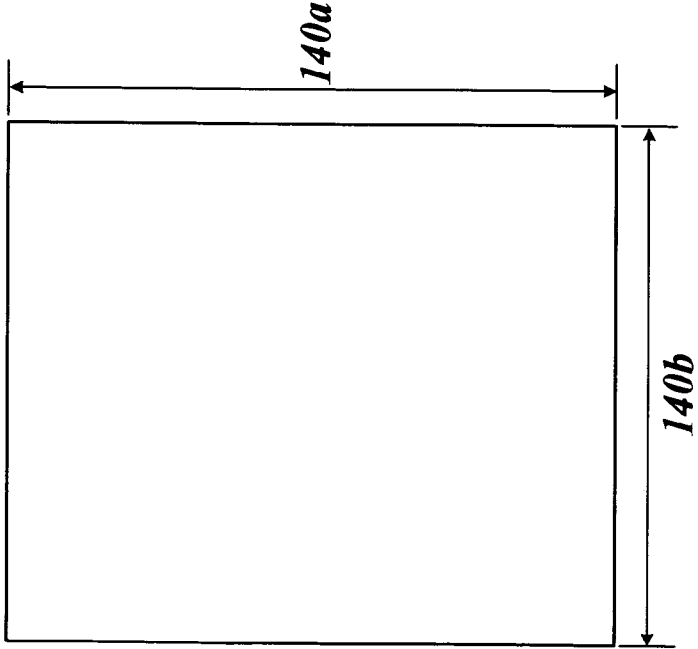

The transmitted image size 146 is an image size (number of pixels) of medical image data in the actual size template data 149 to be transferred to a film output apparatus. As shown in FIG. 11, when the horizontal side of the receive image size 144 is denoted by a reference mark x1, and the vertical side thereof is denoted by a reference mark y1, and the horizontal side of the transmitted image size 146 is denoted by a reference mark x2, and the vertical side thereof is denoted by a reference mark y2, the CPU 11 calculates the number of pixels of the transmitted image size 146 using formulae (10) and (11).

$$\text{Transmitted Image Size (horizontal) } [x2] = \text{Received Image Size (horizontal) } [x1] \quad (10)$$

$$\text{Transmitted Image Size (vertical) } [Y2] = \text{One-Frame Image Region Size (vertical) } [140a] \times \text{Transmitted Image Size (horizontal) } [x2] \div \text{One-Frame Image Region Size (horizontal) } [140b] \quad (11)$$

That is, the horizontal side of the transmitted image size 146 is fixed to the horizontal side of the received image size 144, and the transmitted image size 146 is calculated so that the aspect ratio of the transmitted image size 146 may be the aspect ratio of the one-frame image region size 140.

The expansion or contraction rate 148 is a ratio for adjusting medical image data according to the aspect ratio of the one-frame image region size 140. The CPU 11 calculates the expansion or contraction rate 148 from the received image size 144 and the transmitted image size 146 using a formula (12).

$$\text{Expansion or Contraction Rate } 148 = \text{Transmitted Image Size (vertical) } [Y2] \div \text{One-Frame Image Region Size (horizontal) } [140b] \quad (12)$$

The actual size template data 149 is image data which has been obtained by embedding the received medical image data and the patient information 138 of the image data in the state of being substantially their actual sizes, and by synthesizing them. The CPU 11 re-calculates the image space SP, the tram width W and the character size CS, which have been calculated in conformity with the formulae (1)-(3) described above, and produces the actual size template data 149 using the re-calculated data. More specifically, the following processing is performed.

First, formulae (13)-(15) are calculated.

$$\text{Image Space } SP = \text{Image Space [actual size value]} \times \text{Expansion or Contraction Rate } 148 \quad (13)$$

$$\text{Trim Width } W = \text{Trim Width [actual size value]} \times \text{Expansion or Contraction Rate } 148 \quad (14)$$

$$\text{Character Size } CS \text{ (vertical)} = \text{Character Size [actual size value]} \times \text{Expansion or Contraction Rate } 148 \quad (15)$$

Although the numbers of pixels of the image space, the trim width and the character size are calculated in the first embodiment described above, the actual size values (lengths) of the image space, the trim width and the character size which have been adjusted based on the expansion or contraction rate 148 are calculated in the modification example.

Incidentally, when the image space SP and the trim width W have become smaller than "1 cm", they may be fixedly set to be "1 cm."

Next, the actual size value of the character drawing region AR20 is calculated using formulae (16) and (17).

$$\text{Character Drawing Region } AR20 \text{ (vertical)} = \text{Character Size (height) [actual size value]} \times \text{Number of Character Lines} \quad (16)$$

$$\text{Character Drawing Region } AR20 \text{ (horizontal)} = \text{Image Output Size (horizontal) } 134b \quad (17)$$

Successively, the number of characters (number of characters capable of being output) capable of being drawn in each line in the character drawing region AR20 and the size (actual size template size) of the actual size value of the actual size template data 149 are calculated using formulae (18)-(20).

$$\text{Number of Characters Capable of Being Output} = \text{Character Drawing Region } AR20 \text{ (horizontal)} \div \text{Character Size (width)} \quad (18)$$

$$\text{Actual Size Template Size (horizontal)} = \text{(One-Frame Image Region Size (horizontal) } 140b \times \text{Horizontal Number Of Frames)} + \text{(Trim Width } W \times 2 \times \text{Horizontal Number of Frames)} + \text{(Image Space } Sp \times \text{(Horizontal Number of Frames} - 1)) \quad (19)$$

$$\text{Actual Size Template Size (vertical)} = \text{(One-Frame Image Region Size (vertical) } 140a \times \text{Vertical Number of Frames)} + \text{(Trim Width } W \times 2 \times \text{Vertical Number of Frames)} + \text{(Image Space } Sp \times \text{(Vertical Number of Frames} - 1)) + \text{Character Drawing Region } AR20 \text{ (vertical)} \quad (20)$$

The CPU 11 sets the size of the actual size template data 149 to the size of the actual size template size, and embeds the received medical image data and the patient information 138 of the image data into the actual size template data 149.

Figure 12:
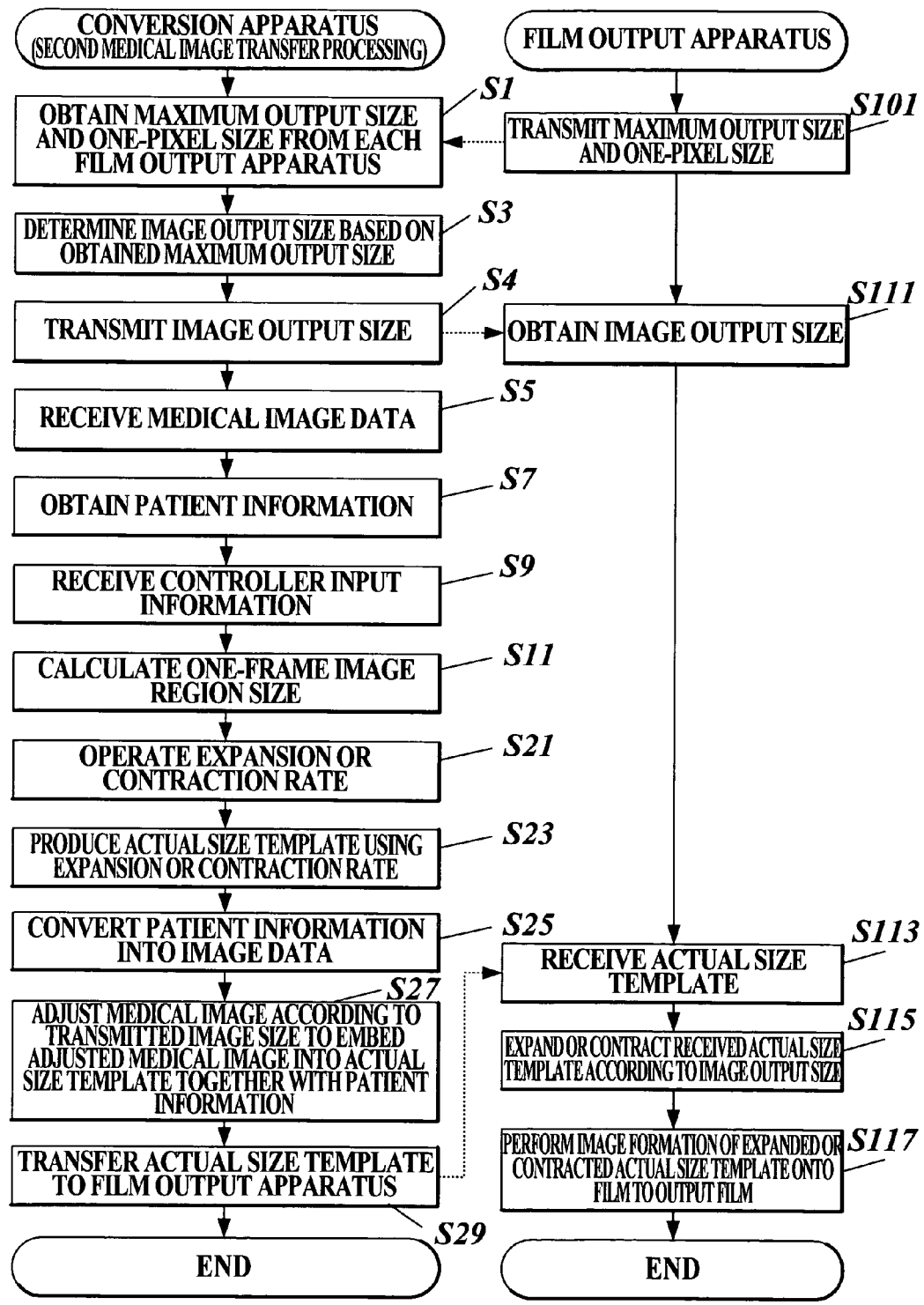
FIG. 12 is a flowchart for illustrating a concrete operation of a medical image output system according to the second embodiment.
Figure 14:
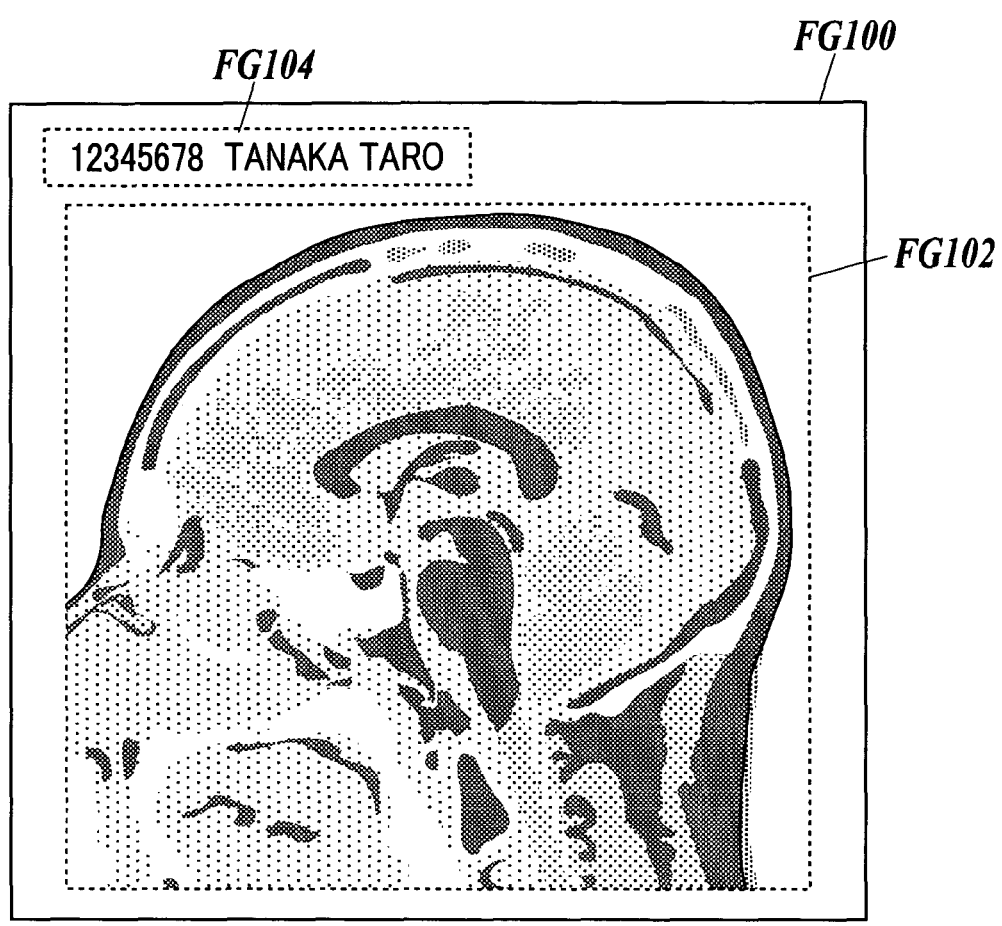
FIG. 14 is a figure showing an example of a medical image.
Figure 15A:
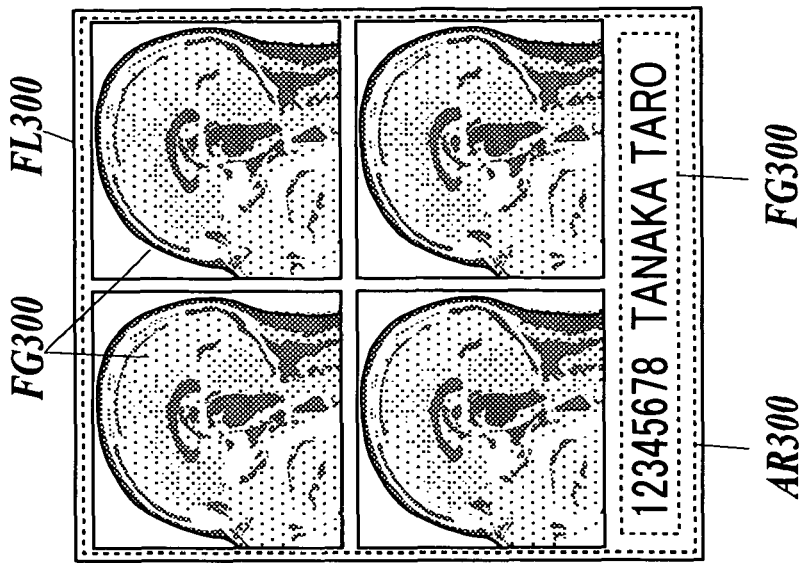
FIGS. 15A, 15B and 15C are figures showing examples of general views of films which respective conventional film output apparatus have outputted.
Figure 15B:
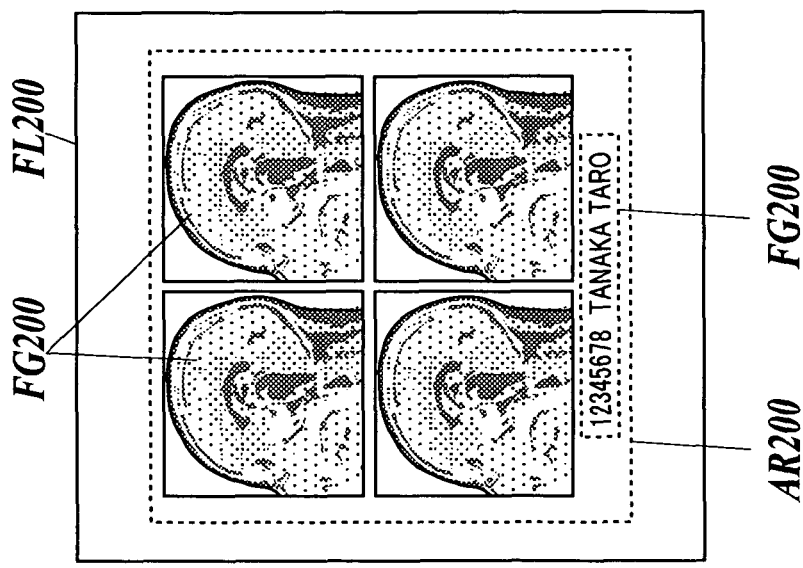
Figure 15C:
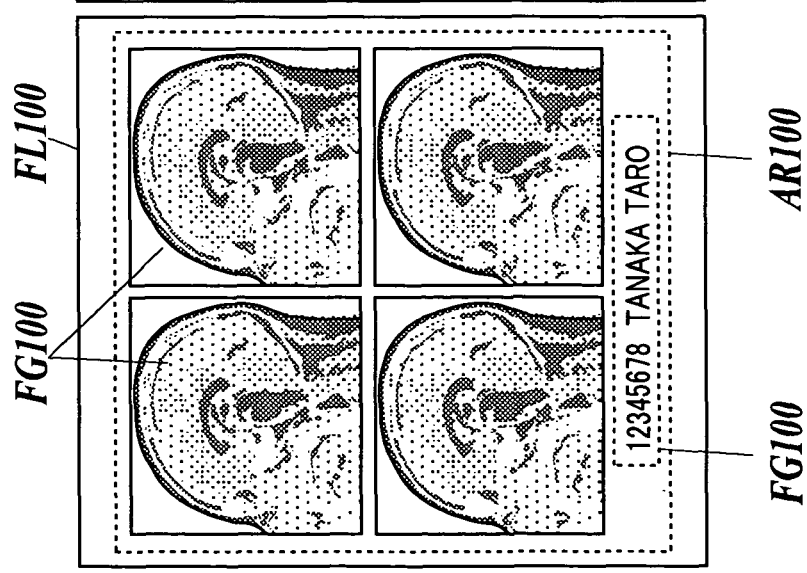

Next, the concrete operation of the medical image output system 100 in the second embodiment is described using the flowchart of FIG. 12. Incidentally, the same marks are given to the same processing steps as those of the flowchart of FIG. 8 described above, and their detailed descriptions are omitted.

First, when the CPU 11 of the conversion apparatus G starts the second medical image transfer processing, the CPU 11 performs the obtainment of the maximum output size and the one-pixel size from each film output apparatus, and the determination of the image output size 134 (Steps S1-S3).

Then, the CPU 11 transmits the determined image output size 134 to each of the film output apparatus F1, F2 and F3 (Step S4), and performs the processing at Steps S5-S11 similarly to the first medical image transfer processing described above (Steps S5-S11). Incidentally, a transmission unit is realized by the processing at Step S4.

The CPU 11 calculates the expansion or contraction rate 148 in accordance with the calculation method described above (Step S21), and produces the actual size template data 149 using the expansion or contraction rate 148 (Step S23). Successively, the CPU 11 adjusts the medical image data according to the transmitted image size 146, and embeds the adjusted medical image data into the actual size template data 149 together with the patient information 138 which has been converted into image data (Step S27). Then, the CPU 11 transmits the actual size template data 149 to the film output apparatus represented by the image transmission destination 130b before ending the second medical image transfer processing.

On the other hand, the film output apparatus transmits the maximum output size 52 and the one-pixel size 54 in response to a request of the conversion apparatus G (Step S101) before receiving the image output size transmitted from the conversion apparatus G to store the received image output size into the storage unit 50 as the received image output size 56 (Step S111). At this time, the film output apparatus realizes a reception unit.

Then, after the CPU 11 has received the actual size template data 149 transmitted from the conversion apparatus G (Step S113), the CPU 11 expands or contracts the actual size template data 149 according to the received image output size 56 (Step S115), and outputs the image based on the data by performing the image formation at the center of the film (Step S117). Incidentally, in the second embodiment, the expansion or contraction unit is realized on the film output apparatus side. Moreover, by the processing at Step S117, an image formation unit is realized.

As described above, according to the second embodiment, the medical image data in the actual size template data 149 which the conversion apparatus G transmits is not the data expanded based on the image output size 134 like the first embodiment described above, but the data the aspect ratio of which is adjusted based on the size of the received image data. Consequently, the data capacity to be transmitted to the film apparatus by the conversion apparatus G can be reduced.

Moreover, generally as long as a film output apparatus of one based on DICOM Standards, the apparatus installs the processing function of the expansion and contraction of image data. Consequently, the processing speed of the whole system of the medical image output system 100 can be raised by performing the expansion or the contraction of medical image data by the film output apparatus.

Moreover, the image formation of the medical image and the patient information of a size in accordance with the image output size is performed on a film on the film output apparatus side. Thereby, even different film output apparatus could output medical images and patient information which have the same size. Consequently, advantages similar to those of the first embodiment can be obtained.

Incidentally, in the present embodiment, although the image output sizes are determined based on the maximum output size of each film output apparatus, for example, a user may operate the controller C to specify the image output sizes. Moreover, in the case of the second embodiment, the specification may be performed on the film output apparatus side. However, when the specified image output size is larger than the image output size of each film output apparatus, it is necessary to notify a user of the fact to urge the user to perform the specification of the image output size again.

Moreover, although the image based on the template data 142 and the actual size template data 149 are subjected to the image formation to set the image at the center of a film, for example, a medical image may be subjected to the image formation after setting a margin of a fixed value (e.g. 2 cm) from the upper end or the lower end of a film. In this case, when the films are superposed on one another by aligning the upper end or the lower end where the margin is formed, the patient information and the medical images do not shift from one another.

Moreover, the size (film size) of the film in which a film output apparatus performs image formation is suitably changeable, and the image output size may be determined according to the film size. More specifically, an output apparatus setting information table 133 of the data configuration as shown in FIG. 13 is stored in the memory 13. According to the diagram, the output apparatus setting information table 133 stores the film sizes such as "A4" or "B4", the maximum output sizes and one-pixel sizes. Moreover, the maximum output sizes to the film sizes are separately associated with the film sizes.

The CPU 11 obtains the maximum output size and the one-pixel size of each film size from each film output apparatus. And the CPU 11 selects the maximum output size corresponding to the film size specified by the operation of the controller C by a user to each film output apparatus, and determines the image output size 134 using the selected maximum output size. Thereby, the sizes of the medical image and the patient information become the same to each specified film. Incidentally, of course, the specification of the film size may be performed by the diagnostic apparatus M.

The present application is based on Japanese Patent Application No. Tokugan 2005-756 filed with Japan Patent Office on Jan. 5, 2005.

What is claimed is:

1. A medical image output system, comprising a medical image transferring apparatus for transferring received medical image data to a plurality of medical image forming apparatuses, each medical image forming apparatus outputting a sheet-like recording medium having an image formable region in which a medical image is formed based on the transferred medical image data;

wherein each of the medical image forming apparatuses includes a storage unit for storing image formable region information representing the image formable region; and wherein the medical image transferring apparatus includes:

an obtaining unit for obtaining the image formable region information stored in the storage unit of each of the plurality of medical image forming apparatuses;

a determination unit for determining an image formation size based on the image formable region information obtained by the obtaining unit;

an expansion or contraction unit for expanding or contracting the received medical image data according to the image formation size determined by the determination unit; and a transfer unit for transferring the medical image data expanded or contracted by the expansion or contraction unit to the medical image forming apparatus.

2. A medical image output system, comprising:

a medical image transferring apparatus for transferring received medical image data to a plurality of medical image forming apparatuses; and a plurality of medical image forming apparatuses for outputting a sheet-like recording medium having an image formable region in which a medical image is formed based on the transferred medical image data;

wherein each of the medical image forming apparatuses includes a storage unit for storing image formable region information representing the image formable region; and wherein the medical image transferring apparatus includes:

an obtaining unit for obtaining the image formable region information stored in the storage unit of each of the plurality of medical image forming apparatus;

a determination unit for determining an image formation size based on the image formable region information obtained by the obtaining unit; and a transmission unit for transmitting the image formation size determined by the determination unit to each of the medical image forming apparatus; and wherein each of the medical image forming apparatuses includes:

a receiving unit for receiving the image formation size transmitted from the transmission unit;

an expansion or contraction unit for expanding or contracting the transferred medical image data according to the image formation size received by the receiving unit; and an image formation unit for performing image formation of the medical image data expanded or contracted by the expansion or contraction unit on the sheet-like recording medium.

3. The medical image output system of claim 1, wherein the determination unit determines an image formation size that fits within all of the image formable regions of the plurality of medical image forming apparatuses based on the image formable region information obtained by the obtaining unit.

4. The medical image output system of claim 3, wherein the image formable region information includes lengths of a vertical side and a horizontal side of the image formable region; and wherein the determination unit selects a minimum vertical side length and a minimum horizontal side length among each of the image formable regions of the plurality of medical image forming apparatuses obtained by the obtaining unit, and determines the selected lengths as an image output size.

5. The medical output system of claim 1, wherein the medical image data includes patient information and a radiography image produced by radiographing a subject.

6. A medical image transfer apparatus for receiving medical image data and transferring the received medical image data to a plurality of medical image forming apparatuses, the medical image transfer apparatus comprising:

an obtaining unit for obtaining image formable region information from each of the plurality of medical image forming apparatuses;

a determination unit for determining an image formation size based on the image formable region information obtained by the obtaining unit;

an expansion or contraction unit for expanding or contracting the received medical image data according to the image formation size determined by the determination unit; and a transfer unit for transferring the medical image data expanded or contracted by the expansion or contraction unit to the medical image forming apparatus.

7. A computer-readable medium storing instructions for making a computer execute a function of receiving medical image data and transferring the received medical image data to a plurality of medical image forming apparatuses, the instructions comprising:

an obtaining function of obtaining image formable region information from each of the plurality of medical image forming apparatuses;

a determining function of determining an image formation size based on the image formable region information obtained by the obtaining function;

an expansion or contraction function of expanding or contracting the received medical image data according to the image formation size determined by the determining function; and a transfer function of transferring the medical image data expanded or contracted by the expansion or contraction function to the medical image forming apparatuses.

* * * * *